(12) United States Patent
Grenier et al.

(10) Patent No.: US 7,838,028 B2
(45) Date of Patent: Nov. 23, 2010

(54) PHARMACEUTICAL TABLET SYSTEM THAT FLOATS ON GASTRIC FLUID FOR MULTIPULSE RELEASE OF ACTIVE SUBSTANCE, AND RESPECTIVE PROCESSES OF PRODUCING SAME AND A CUP-SHAPED ENVELOPE OF SAME

(75) Inventors: Pascal Grenier, Kappelen (FR); Elisabeth Ricchi, Paris (FR); Jacques Quinton, Waldighofen (FR); Guy Vergnault, Saint Louis (FR)

(73) Assignee: Jagotec AG, Muttenz (CH)

( * ) Notice: Subject to any disclaimer, the term of this patent is extended or adjusted under 35 U.S.C. 154(b) by 1142 days.

(21) Appl. No.: 10/473,055

(22) PCT Filed: Mar. 18, 2002

(86) PCT No.: PCT/IB02/00959

§ 371 (c)(1), (2), (4) Date: Mar. 30, 2004

(87) PCT Pub. No.: WO02/085332

PCT Pub. Date: Oct. 31, 2002

(65) Prior Publication Data

US 2004/0166161 A1      Aug. 26, 2004

(30) Foreign Application Priority Data

Mar. 31, 2001   (EP)   ................... 01108252

(51) Int. Cl.
- *A61K 9/20* (2006.01)
- *A61K 9/22* (2006.01)
- *A61K 9/24* (2006.01)
- *A61K 9/28* (2006.01)
- *A61K 9/30* (2006.01)

(52) U.S. Cl. .............. 424/464; 424/465; 424/468; 424/472; 424/474; 424/475

(58) Field of Classification Search ............... 424/464, 424/472
See application file for complete search history.

(56) References Cited

U.S. PATENT DOCUMENTS 3,976,764 A    8/1976   Watanabe et al.

(Continued)

FOREIGN PATENT DOCUMENTS

EP    0 202 159 A2    11/1986

(Continued)

*Primary Examiner*—Humera N Sheikh
(74) *Attorney, Agent, or Firm*—McCormick, Paulding & Huber LLP

(57) ABSTRACT

A tablet system for prolonged floating in or on gastric fluid for releasing therein pharmaceutically active substances in an alternate succession of substance release and no-release periods is made up of a multilayered core placed in a cup-shaped envelope. The core is made up of release layers and no-release layers devoid of pharmaceutically active substance, superposed in alternate succession. The cup-shaped envelope covers bottom and side surfaces of the core while leaving exposed an upper surface of the core. The cup-shaped envelope provides for buoyancy by being formed of a compression-sintered mixture comprising hydrophobic material and inert powdered filler. The hydrophobic material is composed of fatty and/or waxy material capable of being sintered by compression and whose bulk density is lower than gastric fluid density. The powdered filler has a loose powder density that is lower than gastric fluid density.

12 Claims, 3 Drawing Sheets

U.S. PATENT DOCUMENTS

| | | | |
|---|---|---|---|
| 4,101,650 | A | 7/1978 | Umezawa |
| 4,126,672 | A | 11/1978 | Sheth et al. |
| 4,140,755 | A * | 2/1979 | Sheth et al. |
| 4,167,558 | A | 9/1979 | Sheth et al. |
| 4,193,985 | A | 3/1980 | Bechgaard et al. |
| 4,434,153 | A | 2/1984 | Urquhart et al. |
| 4,702,918 | A | 10/1987 | Ushimaru et al. |
| 4,735,804 | A | 4/1988 | Caldwell et al. |
| 4,758,436 | A | 7/1988 | Caldwell et al. |
| 4,767,627 | A | 8/1988 | Caldwell et al. |
| 4,814,178 | A | 3/1989 | Bolton et al. |
| 4,814,179 | A * | 3/1989 | Bolton et al. |
| 4,844,905 | A | 7/1989 | Ichikawa et al. |
| 4,996,058 | A | 2/1991 | Sinnreich |
| 5,002,772 | A | 3/1991 | Curatolo et al. |
| 5,169,639 | A | 12/1992 | Baichwal et al. |
| 5,198,229 | A | 3/1993 | Wong et al. |
| 5,213,794 | A | 5/1993 | Fritsch et al. |
| 5,213,808 | A | 5/1993 | Bar-Shalom et al. |
| 5,232,704 | A | 8/1993 | Franz et al. |
| 5,288,506 | A | 2/1994 | Spickett et al. |
| 5,360,793 | A | 11/1994 | Brooks |
| 5,374,430 | A | 12/1994 | Newton et al. |
| 5,571,533 | A | 11/1996 | Santus et al. |
| 5,626,876 | A | 5/1997 | Muller et al. |
| 5,651,985 | A | 7/1997 | Penners et al. |
| 6,342,249 | B1 * | 1/2002 | Wong et al. |

FOREIGN PATENT DOCUMENTS

| | | |
|---|---|---|
| EP | 0 526 863 A1 | 2/1993 |
| EP | 0 631 775 A1 | 1/1995 |
| EP | 0 669 129 B1 | 8/1995 |
| EP | 0 788 790 A2 | 8/1997 |
| EP | 0788790 * | 8/1997 |
| EP | 0788790 A2 * | 8/1997 |
| EP | 1 074 249 A1 | 2/2001 |
| GB | 1 546 448 | 5/1979 |
| JP | 1016715 | 1/1989 |
| JP | 310615 | 4/1991 |
| JP | 5500668 | 2/1993 |
| JP | 06 024959 A | 2/1994 |
| JP | 6024959 | 2/1994 |
| WO | 91/04015 | 4/1991 |
| WO | 93/24124 | 12/1993 |
| WO | 96/29054 | 9/1996 |
| WO | 97/47285 | 12/1997 |
| WO | 98/31341 | 7/1998 |
| WO | 98/42311 | 10/1998 |
| WO | 98/47506 | 10/1998 |
| WO | 98/52547 | 11/1998 |

* cited by examiner

PHARMACEUTICAL TABLET SYSTEM THAT FLOATS ON GASTRIC FLUID FOR MULTIPULSE RELEASE OF ACTIVE SUBSTANCE, AND RESPECTIVE PROCESSES OF PRODUCING SAME AND A CUP-SHAPED ENVELOPE OF SAME

CROSS REFERENCE TO PRIOR APPLICATIONS

Applicant hereby claims foreign priority under 35 U.S.C. §119 from PCT/IB02/00959 filed 30 Mar. 2002, and European Patent Application No. 01108252.6 filed 31 Mar. 2001, the disclosures of which are herein incorporated by reference.

TECHNICAL FIELD OF THE INVENTION

This invention concerns a pharmaceutical tablet system capable of prolonged floating in or on gastric fluid for releasing therein one or more pharmaceutically active substances in the course of an alternate succession of periods of substance release and no-release, said alternate succession including at least two periods of substance release separated by one period of no-release i.e. of latency. This invention also concerns a process of producing said pharmaceutical tablet system and a process of producing a cup-shaped envelope of said pharmaceutical tablet system.

BACKGROUND ART

For an overall view of the field of the art to which the invention pertains, reference may be made for instance to Moës A. J., "Gastroretentive Dosage Forms", Critical Reviews in Therapeutic Drug Carrier Systems 10(2):143-195 (1993), and also to Singh B. N. et al., "Floating drug delivery systems: an approach to oral controlled drug delivery via gastric retention", Journal of Controlled Release 63(3):35-259 (2000).

Pharmaceutical tablet systems capable of prolonged floating in or on gastric fluid e.g. so as to have a long time of residence in a patient's stomach for releasing therein a pharmaceutically active substance in sustained manner are known in the art. Generally, pharmaceutical forms having a long time of residence in a patient's stomach are of great interest, not only because they allow a local treatment of the patient's stomach wall and more particularly of the gastric mucous membrane, but also and above all because they allow to release active substance in the vicinity of the patient's duodenum, which is a very favourable location of the gastro-intestinal tract where a great many active substances are best absorbed.

There are several approaches for bringing about a prolonged time of residence in the stomach.

A tablet system can be formulated so as to adhere to the gastric mucous membrane (cf. for instance U.S. Pat. No. 5,213,794, U.S. Pat. No. 5,571,533, WO-A-93/24124, WO-A-98/42311, WO-A-98/52547). A major drawback of such adhering systems resides in the difficulty of bringing about that they reliably adhere and remain adherent to the gastric mucous membrane, for the latter is continually undergoing changes and replacement processes and is also subject to the peristalsis i.e. to strong contractions that take place at the stomach wall. In respect of adherence to the gastric mucous membrane no helpful knowledge can be derived from currently used pharmaceutical forms designed to adhere e.g. onto nasal or buccal surfaces, because such forms need to be pressed onto said surfaces at application time, which pressing is not possible onto a patient's gastric mucous membrane, to say nothing of the hazard of the forms getting stuck in the patient's esophagus.

A tablet system can also be formulated to have a high apparent density that, following ingestion, will cause the system to settle in the stomach at the lower portion of the antrum (cf. for instance U.S. Pat. Nos. 4,193,985, 5,374,430). However, the movement of substances contained in the stomach towards the lower portion of the antrum participates in the natural sequence of events related to gastric discharge and hence, pharmaceutical forms formulated so as to settle in the antrum are likely to pass the patient's pylorus either with the bolus (during the digestion process) or together with undigested debris (in the time interval between two successive digestion processes). Thus, to secure the gastroretention of systems formulated so as to have a high apparent density, such systems must additionally be given some properties that will promote the gastroretention, which will raise again the problems already discussed above. Indeed, in EP-A-526862 a granulate is disclosed that not only has a high density but also is given muco-adhesive properties.

A tablet system can also be formulated so as to grow in the stomach, following ingestion, to a size large enough to hinder the system from passing the patient's pylorus even when the latter is open. A great many of these systems are either folded at ingestion time and made to unfold and open out in the stomach following ingestion (cf. for instance EP-A-202159, U.S. Pat. Nos. 4,735,804, 4,758,436, 4,767,627, 5,002,772) or they are made to swell in the stomach following ingestion, for example as a result of gelling (cf. for instance U.S. Pat. Nos. 4,434,153, 5,651,985) or carbon dioxide emission (cf. for instance U.S. Pat. No. 4,996,058, WO-A-98/31341). However, systems formulated to swell could easily pass the patient's pylorus during the latency period that runs from ingestion time until the system has grown to a sufficient size for the gastroretention mechanism to become effective. On the other hand, systems formulated to unfold and open out in the stomach might well be retained permanently in the stomach or even in the esophagus, due to early activation of the deployment mechanism. Each of such failure cases will cause severe secondary effects.

A tablet system can also be formulated with agents that delay or slow down the transit through the stomach, such as lipid-based vehicles (for instance, fatty acids) or depressors of the central nervous system (for instance, serotonine antagonists). These agents bring about a reduction of the stomach motility, which in turn slows down the gastric discharge. Such a way of bringing about gastroretention is most often used in association with other ways (cf. for instance WO-A-97/47285). However, as systems that bring about a reduction of the stomach motility interfere with the whole mechanism of gastric discharge, they are likely to cause digestion problems or worsen them, if already existing. Furthermore, the use of a serotonine antagonist has to comply with pertaining health and drug regulations.

Hence, all known tablet systems of the above mentioned types must be deemed unreliable in respect of providing a prolonged time of residence in the stomach and therefore, they all are unsuitable for providing reliably an alternate succession of periods of substance release and no-release with at least two periods of substance release separated by one period of no-release e.g. when structured in accordance with the teaching of EP-A-788790.

A tablet system can also be formulated to float on the content of the stomach.

The buoyancy of such a tablet system may be provided by means of an initially dense matrix that undergoes gelling in the stomach following ingestion, which causes the matrix to swell and hence, reduces its density (cf. for instance GB-A-1546448, U.S. Pat. Nos. 4,126,672, 4,140,755, 4,167,558, 5,169,639, 5,360,793, WO-A-96/29054); or the buoyancy of such a tablet system may be provided by means of a film or coating that undergoes carbon dioxide emission in the stomach following ingestion, which causes the film or coating to foam (an effect that may be understood as a special type of swelling) and hence, reduces its density (cf. for instance U.S. Pat. Nos. 4,101,650, 4,844,905, WO-A-98/47506); or the buoyancy of such a tablet system may be obtained by providing it right from the start (i.e. before ingestion) with a density that is sufficiently low to keep the tablet system floating in the stomach following ingestion (cf. for instance JP-A-3-101615, U.S. Pat. Nos. 3,976,764, 4,702,918, 4,814,178, 4,814,179, 5,198,229, 5,232,704, 5,288,506, 5,626,876).

Besides the fact that some of these tablet systems formulated to float on the content of the stomach may have their own severe drawbacks, all these systems (with the single exception of the above-mentioned U.S. Pat. No. 4,140,755) only bring about a single period of release of active substance (irrespective of the fact that the active substance may actually consist of a mixture of active compounds). As to the system disclosed in the above-mentioned U.S. Pat. No. 4,140,755, this latter system can only bring about a single immediate release of active substance followed by a single prolonged release of the same active substance.

Thus, none of the above-mentioned tablet systems formulated to float on the content of the stomach is capable of providing reliably a "multipulse release" consisting of an alternate succession of periods of substance release and no-release, which alternate succession would include at least two periods of substance release separated by one period of no-release.

Yet, such a multipulse release capability is highly desirable in a tablet system formulated to float on the content of the stomach, for it would allow a patient to take one single drug unit form to produce a drug plasma level scheme that can only result at present times from administering to the patient two or more standard-type fast-release drug unit forms to be taken in succession at respective predefined time instants separated by respective predefined latency or waiting periods.

Pharmaceutical tablet systems having a multipulse release capability are known in the art.

One type of a pharmaceutical tablet system having a multipulse release capability is known for instance from EP-A-1074249 and is constructed as a multilayered body arranged concentric about a core, which core is fully enclosed within layers that fully enclose one another in succession. The core is the last part of the tablet system that will disappear by dissolution or digestion in gastric fluid or by gastric discharge and hence, to confer prolonged buoyancy to such a tablet system and prevent any early sinking or discharge thereof, at least the core should be formed of lightweight materials. Moreover, in consideration of the possible gastric discharge of the core, a reliable administration can only be attained with a core devoid of any active substance that participates in the desired multipulse release capability, which is not an economical construction because of the necessarily large size of the core.

Another type of a pharmaceutical tablet system having a multipulse release capability is known for instance from WO-A-91/04015, EP-A-631775 or EP-A-788790 and is, basically, made up of planar layers superposed in a stack that is enclosed within an envelope so as to leave at least one outer face of an outer layer of the stack uncovered and unprotected by the envelope. In particular, there is disclosed in EP-A-788790 a pharmaceutical tablet system to be administered by the oral route for releasing one or more pharmaceutically active substances in the course of an alternate succession of periods of substance release and no-release, said alternate succession including at least two periods of substance release separated by one period of no-release. This type of pharmaceutical tablet system is neither intended nor provided for prolonged floating in or on gastric fluid in a patient's stomach.

To nevertheless confer buoyancy to this type of pharmaceutical tablet system, it may be envisaged to use lightweight materials to form the envelope, and this may be expected to be easiest in a tablet system having a cup-shaped envelope and a multilayered core placed therein, as disclosed in EP-A-788790. The cup-shaped envelope is the last part of the tablet system that will disappear by dissolution or digestion in gastric fluid or by gastric discharge and hence, to confer prolonged buoyancy to such a tablet system and prevent any early sinking or discharge thereof, at least the cup-shaped envelope should be formed of lightweight materials. Moreover, in consideration of the possible gastric discharge of the cup-shaped envelope, a reliable multipulse release can only be attained with a cup-shaped envelope devoid of any active substance that participates in the desired multipulse release capability.

Lightweight materials, the use of which may be envisaged in pharmaceutical tablet systems of the above-mentioned type having a multipulse release capability, are known e.g. from the prior art mentioned above. Also, fatty and/or waxy lightweight materials have been used to obtain tablet systems having a low density, for instance according to JP-A-1-016715 that discloses a system having a fatty core made up of fats and oils of density _0.98 and at least one coating layer that contains active substance.

However, these known lightweight materials will not withstand a prolonged floating in or on gastric fluid, as some will dissolve in the gastric fluid, which will cause a progressive loss of buoyancy and subsequent gastric discharge of the tablet system, and others will experience a change of volume e.g. due to gelling that in turn will entail changes of shape allowing the core to eventually become detached from the cup-shaped envelope: in either case the multipulse release characteristics will be unreliable. In a pharmaceutical tablet system of the type mentioned above made up of a stack of superposed layers that is enclosed within an envelope with an outer layer of the stack having an outer face left uncovered and unprotected by the envelope, any poor contact and attachment between the stack of layers and the envelope will allow gastric fluid to infiltrate the system, causing fragility of the tablet system as well as undesirable variations more particularly of the in vivo release rate of the active substance from the innermost i.e. lowermost layer of the stack, producing the so-called "dose dumping". In the particular tablet system having a cup-shaped envelope and a multilayered core placed therein (as disclosed in EP-A-788790) the caused fragility of the tablet system may even allow the core to detach from the cup-shaped envelope.

Also, fats and oils that are currently used (alone or in mixture) in pharmaceutical tablet systems to confer them a density that is lower than unity do not allow tablet production using a compression step of the kind performed in any currently used type of tablet compression apparatus, because of feeding and sticking problems: such fats and oils (whether taken as powders or liquids) have flow properties that do not allow to reliably and evenly fill the press moulds, and during the compression step they stick to the moulding plug and die, impairing the compression efficiency and uniformity.

SUMMARY OF THE INVENTION

Thus, it is an object of the present invention to make available a pharmaceutical tablet system capable of prolonged floating in or on gastric fluid under conditions that are safe for a patient to whom said pharmaceutical tablet system is being administered, for releasing in the patient's stomach one or more pharmaceutically active substances in the course of an alternate succession of periods of substance release and no-release, said alternate succession including at least two periods of substance release separated by one period of no-release i.e. of latency, and which pharmaceutical tablet system does not have the drawbacks of the floating systems of the prior art mentioned above and in particular, should remain floating in or on the gastric fluid in a patient's stomach until the totality of the active substance contained in the pharmaceutical tablet system has been released, irrespective of the fact that said active substance may actually consist of a mixture of active compounds.

To attain this object, according to the present invention there is provided a pharmaceutical tablet system capable of prolonged floating in or on gastric fluid for releasing therein one or more pharmaceutically active substances in the course of an alternate succession of periods of substance release and no-release, said alternate succession including at least two periods of substance release separated by one period of no-release, whereby:

the tablet system is made up of a multilayered core placed in a cup-shaped envelope;

the core is made up of release and no-release layers superposed in alternate succession to form a pile of layers that includes at least two release layers flanking an intermediate no-release layer, each release layer being composed of pharmaceutically acceptable excipient and/or carrier having admixed thereto at least one of said pharmaceutically active substances, each no-release layer being composed of pharmaceutically acceptable excipient and/or carrier devoid of said pharmaceutically active substance;

the cup-shaped envelope covers a bottom surface and side surfaces of the core placed therein while leaving exposed an upper surface of the core;

the cup-shaped envelope provides for buoyancy of the pharmaceutical tablet system with respect to gastric fluid by being formed of a compression-sintered mixture that comprises pharmaceutically acceptable hydrophobic material and pharmaceutically acceptable inert powdered filler;

the hydrophobic material is composed of fatty and/or waxy material capable of being sintered by compression and whose bulk density is lower than gastric fluid density; and the powdered filler having a loose powder density that is lower than gastric fluid density.

Preferably, in a pharmaceutical tablet system according to the present invention the voids may be interstices between grains of the powdered filler, and more preferably, may be generally sealed off from each other by virtue of the hydrophobic material. Also preferably, the voids may be micropores included within the hydrophobic material. Also preferably, the mixture, which the cup-shaped envelope is made of, also includes at least one or more pharmaceutically active agent different from said substances contained in one or more release layers.

A process of producing the above-defined pharmaceutical tablet system involves the steps of coating the powdered filler with the hydrophobic material, preferably by spray-coating performed under vigorous stirring; granulating the resulting coated material; placing a layer of the resulting granulated material into a die; placing a core onto the layer of granulated material within the die; forcing the core into the layer of granulated material within the die, which forcing preferably involves a compression of the tablet system made up of the cup-shaped envelope having the core inserted therein to provide a snug fit between mutually facing bottom and side surfaces of the core and surface portions of the cup-shaped envelope; and removing the resulting tablet system from the die.

A process of producing a cup-shaped envelope of the above-defined pharmaceutical tablet system involves the steps of coating the powdered filler with the hydrophobic material, preferably by spray-coating performed under vigorous stirring; granulating the resulting coated material; placing a layer of the resulting granulated material into a die; forming a cup-shaped recess into the layer of granulated material by forcing a correspondingly shaped body into it within the die; and removing the resulting cup-shaped envelope from the die.

In the pharmaceutical tablet system of the present invention it is the cup-shaped envelope that provides for buoyancy with respect to gastric fluid. The system is constructed to float on gastric fluid at least until the core will have disappeared completely by dissolution or digestion in the gastric fluid and/or subsequent gastric discharge, which also means that all of the active substance will have been fully released. Accordingly, a pharmaceutical tablet system of the present invention will reliably bring about the desired "multipulse release" defined above, irrespective of the fact that the active substance may actually consist of a mixture of active compounds, and irrespective of the duration of the release or no-release i.e. latency periods.

A great advantage of the pharmaceutical tablet system of the present invention is that it allows a patient to take one single drug unit form to reliably produce a drug plasma level scheme equivalent to that which would result from the patient's taking in succession two or more standard-type fast-release drug unit forms at respective predefined time instants separated by respective predefined no-release i.e. latency or waiting periods.

It is particularly advantageous to produce the tablet system by means of the preferred process according to the present invention, which process reliably allows to obtain a snug fit between mutually facing bottom and side surfaces of the core and surface portions of the cup-hasped envelope, which snug fit in turn prevents the core from detaching too early from the cup-shaped envelope and hence, allows the tablet system to provide reliably the desired "multipulse release".

Moreover, the lightweight material used in the pharmaceutical tablet system of the present invention is advantageously well adapted to be compressed in currently used rotary or reciprocating presses without giving rise to any sticking or feeding problems. This finding is quite surprising in view of the difficulties (e.g. unreliable and irregular filling of press moulds, sticking to the moulding plug, impaired compression) that are encountered when fats and oils are used to obtain a low apparent density as taught in the prior art e.g. of JP-A-1-016715 quoted above.

Also, inherent to producing the pharmaceutical tablet system of the present invention according to the above said process, the lightweight material may advantageously be imparted such appropriate hardness and friability properties that will allow an easy handling of intermediate and final products during any subsequent operations such as film coating, packaging etc.

In the process of producing the pharmaceutical tablet system of the invention, the combined provision of using of a hydrophobic material composed of fatty and/or waxy material capable of being sintered by compression, using a powdered filler having a loose powder density that is lower than gastric fluid density and compressing the cup-shaped envelope having the core inserted therein is advantageous in that it results in a snug fit between the core and the cup-shaped envelope. This snug fit seals off the core from the gastric fluid except for the outer face of the core and thus, precludes any poor contact and attachment between the core and the cup-hasped envelope. As no gastric fluid is allowed to infiltrate along the interface between the core and the cup-shaped envelope, the risk of early dissolution or degradation of any other portions of the core than the vicinity if its outer surface is avoided. Such early dissolution would make the no-release or latency period unreliable and/or cause early release of active substance from lower layers of the core, which in turn would lead e.g. to a sustained release instead of a multipulse release of active substance from the pharmaceutical tablet system.

It is a further advantage of the pharmaceutical tablet system of the invention that the hydrophobic material composed of fatty and/or waxy material is sintered by compression, not by melting. Both the degree of sintering and the degree of penetration of the hydrophobic material into the powdered filler can be varied by means of the sintering pressure used, which allows to vary the final properties of the cup-shaped envelope, including the latter's final porosity and thus, the overall porosity of the system.

It is a still further advantage of the pharmaceutical tablet system of the invention that its mechanisms that provide for release and no-release and for buoyancy are independent from each other. This is because no hydrocolloids are used to provide for buoyancy with respect to gastric fluid, the tablet system experiences no change of volume, its buoyancy is not obtained by any gelling of hydrocolloids, and the active substance may be released by other mechanisms that diffusion through a gelled body, which latter mechanism usually leads to a sustained release. All the more, hydrocolloids have a gelling speed that, in a patient's gastric fluid, depends on physiological circumstances such as on the patient's stress, the fluid quantity available in the stomach, the instant filling state of the stomach etc., and in the pharmaceutical tablet system of the invention this is avoided.

DETAILED DESCRIPTION OF THE INVENTION

The present invention will now be explained in closer detail with reference to an exemplary structure of a pharmaceutical tablet system, which structure is of the kind generally known from EP-A-788790. This exemplary structure is constructed cylindrical, and an axial section thereof is illustrated schematically in FIG. 1.

Figure 1:
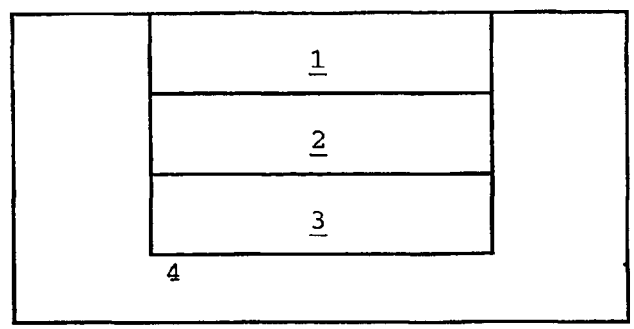
FIG. 1 illustrates an exemplary embodiment of a tablet system according to the present invention with a cylindrical tablet viewed in a schematic axial section.

Generally, the tablet structure illustrated in FIG. 1 comprises a core partially enclosed within an envelope made of lightweight material that provides for buoyancy of the pharmaceutical tablet system with respect to gastric fluid e.g. in a patient's stomach. The core is made up of of three planar layers that are superposed sandwich-like in a generally cylindrical stack having a latency layer 2 located intermediate between active layers 1 and 3. Also, the core is snugly enclosed within a cup-shaped envelope 4 that is generally shaped as a blin-dend hollow cylinder having an axial cylindrical cavity in which the core i.e. the stack of layers 1, 2 and 3 is snugly accommodated in such manner that an outer face of the outer layer 1 of the stack remains uncovered and unprotected by the envelope 4.

The active layers 1 and 3 each are designed to provide release of one or more pharmaceutically active substances and thus, they each contain active substance that is, in the present description and by way of example, diltiazem HCl. The latency layer 2 is designed devoid of active substance so as to provide a period of no-release i.e. of latency.

EXAMPLE 1

1. Preparation of Active Layers

Active layers i.e. layers containing active substance were prepared, each having a weight of 62.50 mg and the following percentage composition (by weight):

| | |
|---|---|
| diltiazem HCl | 30.00% |
| lactose (lactose pulvis H2O, 200 Mesh) from Paul Brem AG, Switzerland | 59.50% |
| sodium croscarmellose Ac-Di-Sol(R), from FMC Corporation, USA | 5.00% |
| polyvinylpyrrolidone Plasdone(R) K29-32, from ISP AG, Switzerland | 4.00% |
| magnesium stearate from Merck, Germany | 1.00% |
| colloidal silica Aerosil(R) 200, from Degussa AG, Hanau, Germany | 0.50% |
| Total composition | 100.00% |

Granulate was prepared in an amount appropriate to allow the production of 12000 cores of the type described above i.e. of 24000 active layers.

Proper amounts of Diltiazem HCl, lactose, sodium croscarmellose and polyvinylpyrolidone were placed in a mixer (from Stephan, Switzerland) and mixed therein. Subsequently the homogeneous mixture was wetted with demineralised water and then further mixed, a process known in the art as a "wet massing" step.

The paste so obtained was dried in a fluidised air bed drier (type Niro-Aeromatic Strea I, 60° C. inlet air temperature, from Aeromatic-Fielder AG, Switzerland). The resulting dried mass was then sized through a sieve granulator (type Frewitt GLA, from Frewitt Fabrique de Machines SA, Switzerland) with a sieve of 0.8 mm aperture, which step produced calibrated granulate.

This calibrated granulate was then placed in a cubic mixer (type Erweka, from Mapag Maschinen AG, Switzerland), added with a proper amount of colloidal silica, and mixed for 15 min at 12 rpm. Then, a proper amount of magnesium stearate was added, and mixing was continued for 5 min. This mixture was then used for the compression step as described below.

2. Preparation of No-release i.e. Latency Layers

Latency layers i.e. layers devoid of active substance were prepared, each having a weight of 100.00 mg and the following percentage composition (by weight):

| | |
|---|---:|
| dibasic calcium phosphate from Emcompress(R), Mendell, USA) | 45.00% |
| lactose (lactose pulvis H2O, 200 Mesh) Lactose Fast Flo(R), from Foremost, USA | 20.00% |
| glyceryl behenate Compritol(R) 888 ATO, from Gattefossé, France | 25.00% |
| polyvinylpyrrolidone Plasdone(R) K29-32, from ISP AG, Switzerland | 8.40% |
| yellow ferric oxide Sicovit(R) Yellow 10E172, from Bascom AG, Switzerland | 0.10% |
| magnesium stearate from Merck, Germany | 1.00% |
| colloidal silica Aerosil(R) 200, from Degussa AG, Hanau, Germany | 0.50% |
| Total composition | 100.00% |

Granulate was prepared in an amount appropriate to allow the production of 15000 cores of the type described above i.e. of 15000 latency layers.

Proper amounts of dibasic calcium phosphate, lactose, glyceryl behenate, polyvinylpyrolidone and yellow ferric oxide were placed in a mixer (from Stephan, Switzerland) and mixed therein. The homogeneous mixture was then wetted with demineralised water and then further mixed in a "wet massing" step.

The paste so obtained was dried in a fluidised air bed drier (type Niro-Aeromatic Strea I, 50° C. inlet air temperature, from Aeromatic-Fielder AG, Switzerland). The resulting dried mass was then sized through a sieve granulator (type Frewitt GLA, from Frewitt Fabrique de Machines SA, Switzerland) with a sieve of 0.8 mm aperture, which step produced calibrated granulate.

This calibrated granulate was then placed in a cubic mixer (type Erweka, from Mapag Maschinen AG, Switzerland), added with a proper amount of colloidal silica, and mixed for 15 min at 12 rpm. Then, a proper amount of magnesium stearate was added, and mixing was continued for 5 min. This mixture was then used for the compression step as described below.

Preparation of Buoyant Material

Buoyant material was prepared, having the following percentage composition (by weight):

| | |
|---|---:|
| hydrogenated castor oil Cutina HR(R), from Impag AG, Switzerland | 70.00% |
| magnesium aluminometasilicate Neusilin UFL(R), from Gustav Parmentier, Germany | 12.25% |
| microcrystalline cellulose Avicel(R) pH 101, from Selectchemie AG, Switzerland | 12.25% |
| gelatine from Merck, Germany | 5.00% |
| magnesium stearate from Merck, Germany | 0.50% |
| Total composition | 100.00% |

In the above composition eventually used for preparing the cup-shaped envelope, cf. below, the hydrophobic material is hydrogenated castor oil and the inert powdered filler is magnesium aluminometasilicate.

Granulate was prepared in an amount appropriate to allow the production of 1000 buoyant cup-shaped envelopes each having a weight of 500.00 mg appropriate to enclose 1000 cores so as to manufacture 1000 tablets.

Proper amounts of hydrogenated castor oil, magnesium aluminometasilicate and cellulose microcrystalline were placed in a high shear mixer (type Niro-Fielder PP1, from Aeromatic-Fielder AG, Switzerland). The homogeneous mixture was then wetted with a gelatine solution made up of gelatine previously dissolved in demineralised water and then further mixed in a "wet massing" step.

The paste so obtained was dried in a fluidised air bed drier (type Niro-Aeromatic Strea I, 50° C. inlet air temperature, from Aeromatic-Fielder AG, Switzerland). The resulting dried mass was then sized through a sieve granulator (type Frewitt GLA, from Frewitt Fabrique de Machines SA, Switzerland) with a sieve of 0.8 mm aperture, which step produced calibrated granulate.

This calibrated granulate was then placed in a cubic mixer (type Erweka, from Mapag Maschinen AG, Switzerland), added with a proper amount of colloidal silica, and mixed for 10 min at 12 rpm. This mixture was then used for the compression step as described below.

Preparation of Cores

Cores were prepared by means of a rotating three layer press (type Manesty LP39, from Keyser Mackay, Switzerland) equipped with circular convex punches having a diameter of 7.0 mm, operating on the granulates prepared as described above with bulk active layer material in the first and third filling hoppers and bulk latency layer material in the second filling hopper.

Application of Buoyancy Conferring Layers Onto Cores

The cores previously prepared as described above were press-coated with the buoyant material prepared as described above by means of a single punch machine (type Korsch, from Korsch Maschinenfabrik, Germany) equipped with dies and circular convex punches having a diameter of 13.0 mm. The die was filled with an exact quantity of the buoyant material and then the core was placed manually in the die and centred. Subsequently, the compression step was then performed.

The resulting tablets had a thickness of 7.10 mm and a hardness of about 75N.

Results

To determine the in vitro release characteristics of the tablets described above, a standard equipment was used as defined and described in United States Pharmacopoeia USP XXIII, chapter 711, page 1792, paragraph "Apparatus 2". This equipment had a stirring paddle comprised of a blade and a shaft and was operated at 100 rpm. Dissolution was investigated at 37° C. in 600 ml of a dissolution medium made up of 0.1M acetate buffer of pH 4.5. The release of the active substance (diltiazem HCl) was monitored by UV spectrophotometry at 278 nm for 6 individual samples and additionally, as a reference, for the dissolution medium taken alone i.e. devoid of any tablet material.

Figure 2:
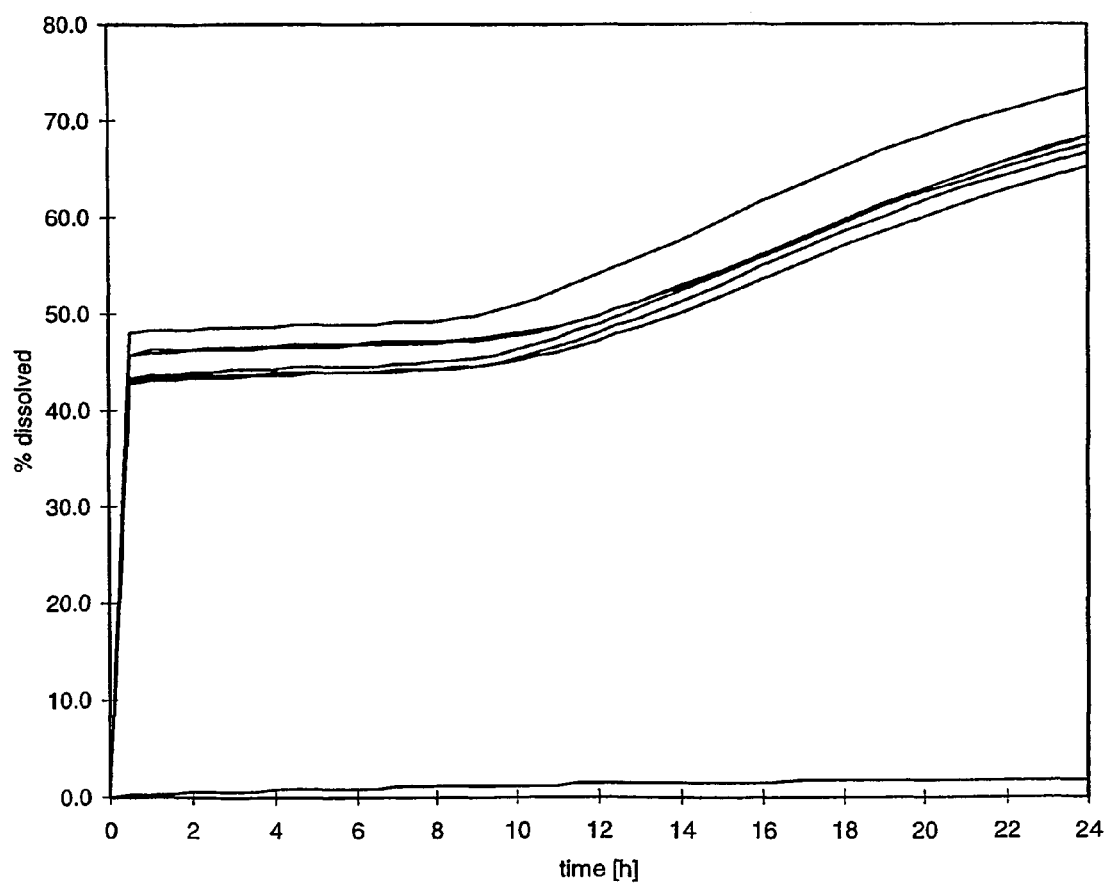
FIG. 2 illustrates in vitro release characteristics of a tablet system according to FIG. 1 with a composition according to Example 1.

The results are illustrated in FIG. 2 as respective time profile diagrams for the 6 tablet samples and the reference. The reference diagram showed that the dissolution medium taken alone i.e. devoid of any tablet material did not bias the results or generate any artifacts. The in vitro release characteristics of all 6 tablets appeared to form a well grouped family that was well separated from the reference characteristic which appeared in the lowest part of the diagram.

In each instance, the following was observed on the in vitro release characteristics:

The first release of active substance takes place within a release period of less than a one hour duration.

The no-release period appears as a well-defined time interval observed between the end of the first release and the start of the second release, having a duration of more than 8 hours in each instance.

The second release of active substance is observed to produce a controlled release.

During the course of the dissolution the tablet system was monitored visually and observed to remain buoyant for the whole duration of the experiment.

EXAMPLE 2

1. Preparation of Active Layers

Active layers i.e. layers containing active substance were prepared, each having a weight of 62.50 mg and the following percentage composition (by weight):

| | |
|---|---|
| diltiazem HCl | 30.00% |
| lactose (lactose pulvis H2O, 200 Mesh) from Paul Brem AG, Switzerland | 34.50% |
| sodium croscarmellose Ac-Di-Sol$^{(R)}$, from FMC Corporation, USA | 5.00% |
| sodium hydrogen carbonate from CFS, Switzerland | 15.00% |
| polyvinylpyrrolidone Plasdone$^{(R)}$ K29-32, from ISP AG, Switzerland | 4.00% |
| citric acid from Merck, Germany | 10.00% |
| magnesium stearate from Merck, Germany | 1.00% |
| colloidal silica Aerosil$^{(R)}$ 200, from Degussa AG, Hanau, Germany | 0.50% |
| Total composition | 100.00% |

Granulate was prepared in an amount appropriate to allow the production of 11000 cores of the type described above i.e. of 22000 active layers, using the same procedure as described above under Example 1 applied to proper amounts, first of diltiazem HCl, lactose, sodium croscarmellose, sodium hydrogen carbonate and polyvinylpyrrolidone, and then of colloidal silica and citric acid, placed in the respective mixer.

Preparation of No-release i.e. Latency Layers

Latency layers i.e. layers devoid of active substance were prepared, each having a weight of 70.00 mg and the following percentage composition (by weight):

| | |
|---|---|
| dibasic calcium phosphate from Emcompress$^{(R)}$, Mendell, USA) | 37.50% |
| lactose (lactose pulvis H2O, 200 Mesh) Lactose Fast Flo$^{(R)}$, from Foremost, USA | 33.34% |
| glyceryl behenate Compritol$^{(R)}$ 888 ATO, from Gattefossé, France | 20.83% |
| polyvinylpyrrolidone Plasdone$^{(R)}$ K29-32, from ISP AG, Switzerland | 7.00% |
| yellow ferric oxide Sicovit$^{(R)}$ Yellow 10E172, from Bascom AG, Switzerland | 0.08% |
| magnesium stearate from Merck, Germany | 0.83% |
| colloidal silica Aerosil$^{(R)}$ 200, from Degussa AG, Hanau, Germany | 0.42% |
| Total composition | 100.00% |

Granulate was prepared in an amount appropriate to allow the production of 2150 cores of the type described above i.e. of 2150 latency layers, using the same procedure as described above under Example 1 applied to proper amounts, first of dibasic calcium phosphate, lactose, glyceryl behenate, polyvinylpyrrolidone and yellow ferric oxide, and then of colloidal silica, placed in the respective mixer.

Preparation of Buoyant Material

Buoyant material was prepared, having the following percentage composition (by weight):

| | |
|---|---|
| hydrogenated castor oil Cutina HR$^{(R)}$, from Impag AG, Switzerland | 70.00% |
| magnesium aluminometasilicate Neusilin UFL$^{(R)}$, from Gustav Parmentier, Germany | 22.00% |
| gelatine from Merck, Germany | 5.00% |
| hydrogenated cottonseed oil from Merck, Germany | 3.00% |
| Total composition | 100.00% |

In the above composition eventually used for preparing the cup-shaped envelope, cf. below, the hydrophobic material is a mixture of hydrogenated castor oil and hydrogenated cottonseed oil, and the inert powdered filler is magnesium aluminometasilicate.

Granulate was prepared in an amount appropriate to allow the production of 300 buoyancy conferring cup-hasped envelopes each having a weight of 500.00 mg appropriate to enclose 300 cores so as to manufacture 300 tablets, using the same procedure as described above under Example 1 applied to proper amounts, first of hydrogenated castor oil and magnesium aluminometasilicate, and then of colloidal silica, placed in the respective mixer.

4. Preparation of Cores

Cores were prepared by means of a single punch machine (type Korsch, from Korsch Maschinenfabrik, Germany) equipped with dies and circular flat punches having a diameter of 7.0 mm. The die was filled with exact quantities of the granulates prepared above, each corresponding to the respective layers. The compression step resulted in cores having a thickness of 3.90 mm and a hardness of about 50N.

5. Application of Buoyancy Conferring Cup-shaped envelopes onto cores

The cores previously prepared as described above were press-coated with the buoyant material prepared as described above, using the same procedure as described above under Example 1. The compression step resulted in tablets having a thickness of 7.10 mm and a hardness of about 75N.

6. Results

The in vitro release characteristics of the tablets described above were determined, using the same procedure as described above under Example 1 except for monitoring the release of the active substance (diltiazem HCl) by UV spectrophotometry at 240 nm for 5 individual samples.

Figure 3:
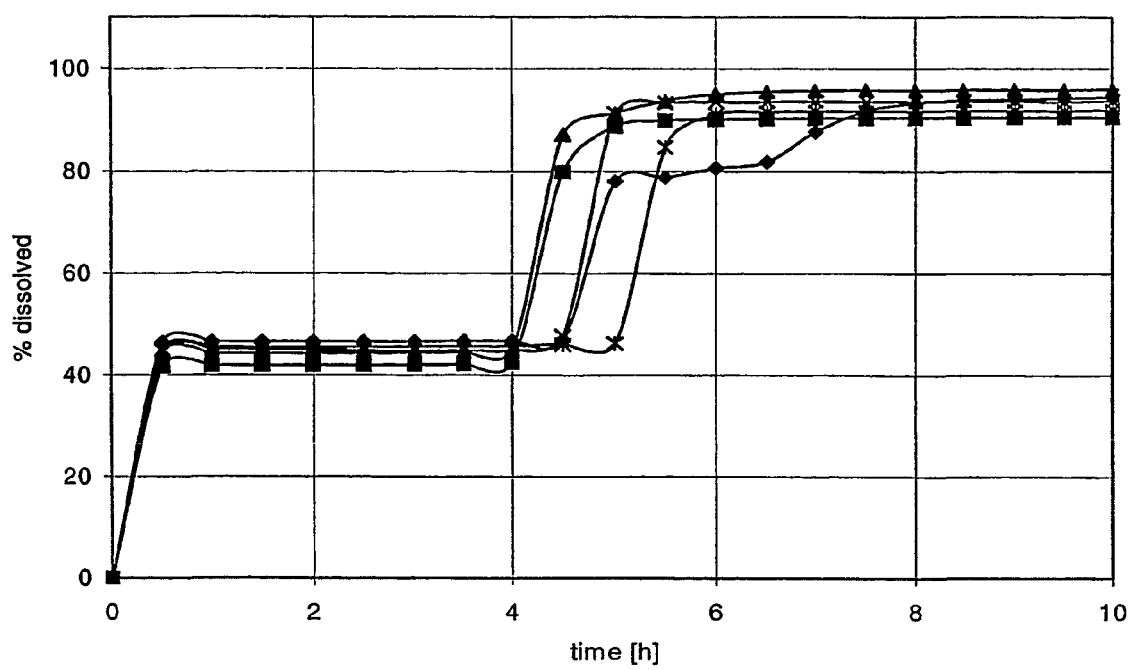
FIG. 3 illustrates in vitro release characteristics of a tablet system according to FIG. 1 with a composition according to Example 2.

The results are illustrated in FIG. 3 as respective time profile diagrams for the 5 tablet samples. The in vitro release characteristics of all 5 tablets appeared to form a well grouped family.

In each instance, the following was observed on the in vitro release characteristics:

The first release of active substance takes place within a release period of less than a one hour duration.

The no-release period appears as a well-defined time interval observed between the end of the first release and the start of the second release, having a duration of more than 4 hours in each instance.

The second release of active substance takes place within a release period of less than a one hour duration.

During the course of the dissolution the tablet system was monitored visually and observed to remain buoyant for the whole duration of the experiment, which duration largely exceeded the time required to release the tablet system's whole content of active substance.

EXAMPLE 3

1. Preparation of Active Layers

Active layers i.e. layers containing active substance were prepared, using the same procedure as described above under Example 1.

2. Preparation of No-release i.e. Latency Layers

Latency layers i.e. layers devoid of active substance were prepared, each having a weight of 100.00 mg and the following percentage composition (by weight):

| | |
|---|---|
| dibasic calcium phosphate from Emcompress$^{(R)}$, Mendell, USA) | 43.00% |
| lactose (lactose pulvis H2O, 200 Mesh) Lactose Fast Flo$^{(R)}$, from Foremost, USA | 30.00% |
| sodium croscarmellose Ac-Di-Sol$^{(R)}$, from FMC Corporation, USA | 2.00% |
| glyceryl behenate Compritol$^{(R)}$ 888 ATO, from Gattefossé, France | 15.00% |
| polyvinylpyrrolidone Plasdone$^{(R)}$ K29-32, from ISP AG, Switzerland | 8.40% |
| yellow ferric oxide Sicovit$^{(R)}$ Yellow 10E172, from Bascom AG, Switzerland | 0.10% |
| magnesium stearate from Merck, Germany | 1.00% |
| colloidal silica Aerosil$^{(R)}$ 200, from Degussa AG, Hanau, Germany | 0.50% |
| Total composition | 100.00% |

Granulate was prepared in an amount appropriate to allow the production of 1500 cores of the type described above i.e. of 1500 latency layers, using the same procedure as described above under Example 1 applied to proper amounts, first of dibasic calcium phosphate, lactose, sodium croscarmellose, glyceryl behenate, polyvinylpyrrolidone and yellow ferric oxide, and then of magnesium stearate and colloidal silica, placed in the respective mixer.

3. Preparation of Buoyant Material

Buoyant material was prepared, using the same procedure as described above under Example 1, leading to the same composition eventually used for preparing the cup-shaped envelope, cf. below, in which the hydrophobic material is hydrogenated castor oil and the inert powdered filler is magnesium aluminometasilicate.

4. Preparation of Cores

Cores were prepared, using the same procedure as described above under Example 2, to result in cores having a thickness of 4.25 mm and a hardness of about 50N.

5. Application of Buoyancy Conferring Cup-shaped Envelopes Onto Cores

The cores previously prepared as described above were press-coated with the buoyant material prepared as described above, using the same procedure as described above under Example 1. The compression step resulted in tablets having a thickness of 7.05 mm and a hardness of about 105N.

6. Results

The in vitro release characteristics of the tablets described above were determined, using the same procedure as described above under Example 2 except for monitoring the release of the active substance (diltiazem HCl) for 6 individual samples.

Figure 4:
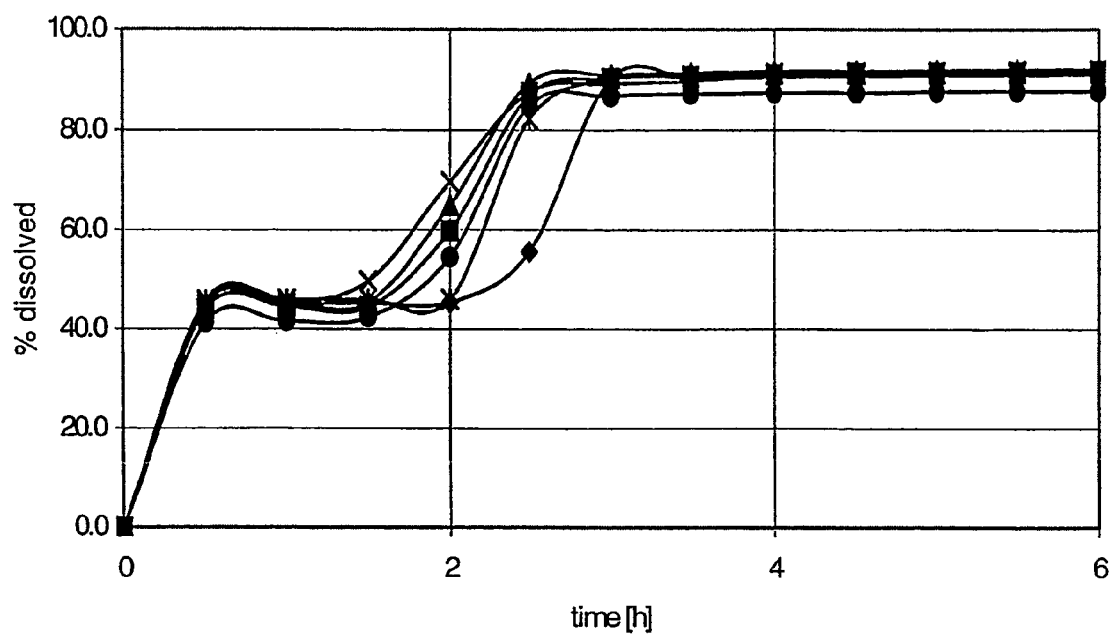
FIG. 4 illustrates in vitro release characteristics of a tablet system according to FIG. 1 with a composition according to Example 3.

The results are illustrated in FIG. 4 as respective time profile diagrams for the 6 tablet samples. The in vitro release characteristics of all 6 tablets appeared to form a well grouped family.

In each instance, the following was observed on the in vitro release characteristics:

The first release of active substance takes place within a release period of less than a one hour duration.

The no-release period appears as a well-defined time interval observed between the end of the first release and the start of the second release, having a duration of more than 2 hours in each instance.

The second release of active substance takes place within a release period of less than a one hour duration.

During the course of the dissolution the tablet system was monitored visually and observed to remain buoyant for the whole duration of the experiment, which duration largely exceeded the time required to release the tablet system's whole content of active substance.

SUMMARY OF EXPERIMENTAL RESULTS

In each instance of the Examples, in the composition eventually used for preparing the cup-shaped envelope the inert powdered filler is magnesium aluminometasilicate and the hydrophobic material is hydrogenated castor oil (in Example 1 and Example 3) or a mixture of hydrogenated castor oil and hydrogenated cottonseed oil (in Example 2).

In each instance and for all three Examples, the first release of active substance takes place within a release period of less than a one hour duration.

In each instance, the no-release period appears to be a well-defined time interval observed between the end of the first release and the start of the second release, having a duration of more than 8 hours in each instance of Example 1, 4 hours in each instance of Example 2, and 2 hours in each instance of Example 3.

In each instance, the second release of active substance is observed to produce a controlled release having a prolonged duration (sustained release) in each instance of Example 1, and in contrast a duration of less than one hour in each instance of Example 2 and Example 3.

During the course of the dissolution the tablet system was monitored visually and observed to remain buoyant for the whole duration of the experiment, which duration largely exceeded the time required to release the tablet system's whole content of active substance in each instance of Example 2 and Example 3.

The invention claimed is:

1. A pharmaceutical tablet system capable of prolonged floating in or on gastric fluid for releasing therein one or more pharmaceutically active substances in the course of an alternate succession of periods of substance release and no-release, said alternate succession having at least two periods of substance release separated by one period of no-release, whereby the tablet system is made up of a multilayered core placed in a cup-shaped envelope, the core is made up of release and no-release layers superposed in alternate succession to form a pile of layers that has at least two release layers flanking an intermediate no-release layer, each release layer being composed of pharmaceutically acceptable excipient and/or carrier having admixed thereto at least one of said pharmaceutically active substances, each no-release layer being composed of pharmaceutically acceptable excipient and/or carrier devoid of said pharmaceutically active substance, the cup-shaped envelope covers a bottom surface and side surfaces of the core placed therein while leaving exposed an upper surface of the core, characterized in that the cup-shaped envelope provides for buoyancy of the pharmaceutical tablet system with respect to gastric fluid by being formed of a compression-sintered mixture with voids, the mixture being comprised by buoyancy-providing materials in the form of a pharmaceutically acceptable hydrophobic material and a pharmaceutically acceptable inert powdered filler, the hydrophobic material being composed of fatty and/or waxy material capable of being sintered by compression and whose bulk density is lower than gastric fluid density, and the powdered filler having a loose powder density that is lower than gastric fluid density, the powdered filler consisting of magnesium aluminometasilicate; and the buoyancy-providing materials of the cup-shaped envelope being incorporated in the finished pharmaceutical tablet system in the range of 69 to 72 percent by weight.

2. A pharmaceutical tablet system according to claim 1, in which the voids are interstices between grains of the powdered filler.

3. A pharmaceutical tablet system according to claim 2, in which the voids generally are sealed off from each other by virtue of the hydrophobic material.

4. A pharmaceutical tablet system according to claim 1, in which the voids are micropores included within the hydrophobic material.

5. A pharmaceutical tablet system according to claim 1, in which the cup-shaped envelope is comprised of a mixture that includes at least one or more pharmaceutically active agents different from said substances contained in one or more of the release layers.

6. A process of producing a pharmaceutical tablet system capable of prolonged floating in or on gastric fluid for releasing therein one or more pharmaceutically active substances in the course of an alternate succession of periods of substance release and no-release, said alternate succession including at least two periods of substance release separated by one period of no-release, whereby the tablet system is made up of a multilayered core placed in a cup-shaped envelope, the core is made up of release and no-release layers superposed in alternate succession to form a pile of layers that includes at least two release layers flanking an intermediate no-release layer, each release layer being composed of pharmaceutically acceptable excipient and/or carrier having admixed thereto at least one of said pharmaceutically active substances, each no-release layer being composed of pharmaceutically acceptable excipient and/or carrier devoid of said pharmaceutically active substance, the cup-shaped envelope covers a bottom surface and side surfaces of the core placed therein while leaving exposed an upper surface of the core, the cup-shaped envelope provides for buoyancy of the pharmaceutical tablet system with respect to gastric fluid by being formed of a compression-sintered mixture with voids, the mixture being comprised by buoyancy-providing materials in the form of a pharmaceutically acceptable hydrophobic material and pharmaceutically acceptable inert powdered filler, the hydrophobic material being composed of fatty and/or waxy material capable of being sintered by compression and whose bulk density is lower than gastric fluid density, and the powdered filler having a loose powder density that is lower than gastric fluid density, the powdered filler consisting of magnesium aluminometasilicate; and the buoyancy-providing materials of the cup-shaped envelope being incorporated in the finished pharmaceutical tablet system in the range of 69 to percent 72 by weight, the method comprising the steps of:

coating the powdered filler with the hydrophobic material;

granulating the resulting coated material; placing a layer of the resulting granulated material into a die;

placing the core onto the layer of granulated material within the die;

forcing the core into the layer of granulated material within the die; and removing the resulting tablet system from the die.

7. A process according to claim 6, in which the step of forcing the core into the layer of granulated material within the die involves a compression of the tablet system made up of the cup-shaped envelope having the core inserted therein to provide a snug fit between mutually facing bottom and side surfaces of the core and surface portions of the cup-shaped envelope.

8. A process of producing a cup-shaped envelope of a pharmaceutical tablet system involving the following steps:

capable of prolonged floating in or on gastric fluid for releasing therein one or more pharmaceutically active substances in the course of an alternate succession of periods of substance release and no-release, said alternate succession including at least two periods of substance release separated by one period of no-release, whereby the tablet system is made up of a multilayered core placed in a cup-shaped envelope, the core is made up of release and no-release layers superposed in alternate succession to form a pile of layers that includes at least two release layers flanking an intermediate no-release layer, each release layer being composed of pharmaceutically acceptable excipient and/or carrier having admixed thereto at least one of said pharmaceutically active substances, each no-release layer being composed of pharmaceutically acceptable excipient and/or carrier devoid of said pharmaceutically active substance, the cup-shaped envelope covers a bottom surface and side surfaces of the core placed therein while leaving exposed an upper surface of the core, the cup-shaped envelope provides for buoyancy of the pharmaceutical tablet system with respect to gastric fluid by being formed of a compression-sintered mixture with voids, the mixture being comprised by buoyancy-providing materials in the form of a pharmaceutically acceptable hydrophobic material and pharmaceutically acceptable inert powdered filler, the hydrophobic material being composed of fatty and/or waxy material capable of being sintered by compression and whose bulk density is lower than gastric fluid density, and the powdered filler having a loose powder density that is lower than gastric fluid density, the powdered filler consisting of magnesium aluminometasilicate; and the buoyancy-providing materials of the cup-shaped envelope being incorporated in the finished pharmaceutical tablet system in the range of 69 to 72 percent by weight, the method comprising:

coating the powdered filler with the hydrophobic material;

granulating the resulting coated material; placing a layer of the resulting granulated material into a die;

forming the cup-shaped recess into the layer of granulated material by forcing a correspondingly shaped body into it within the die; and removing the resulting cup-shaped envelope from the die.

9. A process according to claim 6, in which the step of coating the powdered filler with the hydrophobic material comprises the step of spray-coating performed under vigorous stirring.

10. A process according to claim 8, in which the step of coating the powdered filler with the hydrophobic material comprises the step of spray-coating performed under vigorous stirring.

11. A pharmaceutical tablet system according to claim 1, wherein said two periods of substance release separated by one period of no-release comprise:

a first release period being less than one hour;

a period of no-release lasting longer than the first release period; and a second release period having a prolonged duration.

12. A pharmaceutical tablet system according to claim 1, wherein said two periods of substance release separated by one period of no-release comprise:

a first release period being less than one hour;

a period of no-release lasting longer than the first release period; and a second release period having a duration of less than one hour.

* * * * *